United States Patent [19]

Puckette et al.

[11] Patent Number: 4,879,416

[45] Date of Patent: Nov. 7, 1989

[54] PREPARATION OF BIDENTATE LIGANDS

[75] Inventors: Thomas A. Puckette; Thomas J. Devon; Gerald W. Phillips; Jerome L. Stavinoha, all of Longview, Tex.

[73] Assignee: Eastman Kodak Company, Rochester, N.Y.

[21] Appl. No.: 123,407

[22] Filed: Nov. 23, 1987

[51] Int. Cl.$^4$ .............. C07F 9/02; C07F 9/66
[52] U.S. Cl. ...................... 568/13; 568/14; 568/15; 568/17; 568/764; 568/815; 556/70; 556/71; 570/185; 570/191; 570/196; 564/384; 564/386
[58] Field of Search ............ 556/70, 71; 568/13, 568/14, 15, 17, 764, 815; 570/185, 191, 196; 564/384, 386

[56] References Cited

U.S. PATENT DOCUMENTS

| | | | |
|---|---|---|---|
| 3,239,566 | 3/1966 | Slaugh et al. | 260/604 |
| 3,527,809 | 9/1970 | Pruett et al. | 260/604 |
| 3,539,622 | 11/1970 | Heck | 260/515 |
| 3,636,168 | 1/1972 | Josephson | 260/645 |
| 3,748,350 | 7/1973 | Josephson | 260/475 |
| 4,105,705 | 8/1978 | Lareck | 260/668 |
| 4,138,420 | 2/1979 | Unruh et al. | 260/439 |
| 4,139,565 | 2/1979 | Unruh et al. | 260/604 |
| 4,152,344 | 5/1979 | Unruh | 260/439 |
| 4,169,861 | 10/1979 | Hughes | 260/604 |
| 4,193,943 | 3/1980 | Unruh et al. | 260/604 |
| 4,201,728 | 5/1980 | Hughes | 568/454 |
| 4,221,744 | 9/1980 | Unruh | 568/454 |
| 4,229,381 | 10/1980 | Ogata et al. | 568/454 |
| 4,263,466 | 4/1981 | Colon et al. | 585/421 |
| 4,326,989 | 4/1982 | Colon et al. | 252/429 |
| 4,694,109 | 9/1987 | Devon et al. | 568/454 |
| 4,760,194 | 7/1988 | Phillips et al. | 568/454 |

OTHER PUBLICATIONS

Kende, Liebeskind & Braitsch, Tetrahedron Letters, pp. 3375–3378 (1975).
Tamao, et al., Bulletin of the Chemical Society of Japan, vol. 49, pp. 1958–1969, (1976).
Zembayashi, Tamao, Yoshida & Kumada, Tetrahedron Letters, pp. 4089–4092, (1977).
Colon & Kelsey, Journal of Organic Chemistry, vol. 51, pp. 2627–2637 (1986).
Wittenberg & Gilman, Journal of Organic Chemistry, vol. 23, pp. 1063–1065 (1958).
Bailey & Erickson, Organic Synthesis, vol. 41, pp. 41–45, 46–48, (1961).
Rieke & Bales, Journal of the American Chemical Society, vol. 96, pp. 1775–1781 (1974).
Morrison, R. T., et al., Organic Chemistry, 3rd Ed., Allyn and Bacon, Inc. Boston MA, ©1973, pp. 312–313, 455.
Barton, D. et al., Comprehensive Organic Chemistry, Pergamon Press, New York, ©1979, p. 958.
March Jr., Advanced Organic Chemistry, 2nd Ed., McGraw-Hill Book Company, New York, p. 378, ©1977.

Primary Examiner—H. M. S. Sneed
Assistant Examiner—George R. Fourson
Attorney, Agent, or Firm—S. E. Reiter; William P. Heath, Jr.

[57] ABSTRACT

The process for preparing a bidentate ligand comprising the steps, (1) contacting with ozone under ozonolysis conditions a suspension in a hydroxylic reaction medium of phenanthrene or a phenanthrene derivative to form an ozonated intermediate, (2) contacting said ozonated intermediate with a reducing agent under conditions appropriate to form the corresponding diol, (3) contacting said diol with a latent displaceable functional group under conditions appropriate to convert the diol to the corresponding difunctional biaryl compound, and (4) contacting said difunctional biaryl compound, with an anion of N, P, As, Sb or Bi under conditions appropriate to form the desired bidentate ligand.

21 Claims, No Drawings

PREPARATION OF BIDENTATE LIGANDS

DESCRIPTION

This invention relates to the preparation of bidentate ligands which are useful, for example, in the formation of low pressure hydroformylation catalysts.

BACKGROUND OF THE INVENTION

Bidentate ligands have recently been shown to be very effective for the preparation of organometallic catalysts, such as for example, low pressure hydroformylation catalysts wherein the bidentate ligands are coordinated with rhodium. While a variety of bidentate ligands are useful for such chemical conversions as hydroformylation, their synthesis is often difficult, involving numerous reaction steps, one or more of which give low product yields. The net result is that the target bidentate ligands are obtained in low overall yields and are expensive to prepare.

In order to bidentate ligands such as:

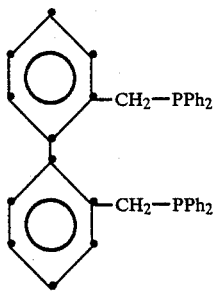

to come into more widespread use, efficient means for the preparation of such bidentate ligands will need to be developed.

OBJECTS OF THE INVENTION

It is, therefore, an object of the present invention to develop improved methods for the preparation of bis(-dihydrocarbylphosphinomethyl)biphenyl-type bidentate ligands.

This and other objects will become apparent from inspection of the detailed description and claims which follow.

STATEMENT OF THE INVENTION

In accordance with the present invention, we have discovered that bis(dihydrocarbylphosphinomethyl)-biphenyl-type compounds can be prepared in high purity and good yield by a several step reaction sequence starting with phananthrene or derivatives thereof. The resulting diphosphine compounds are useful as bidentate ligands in combination with a wide variety of active metal species. For example, when employed in combination with rhodium, the bis(dihydrocarbylphosphinomethyl)-biphenyl-type compounds prepared in accordance with the present invention are useful as components of low pressure hydroformylation processes. Such catalyst systems produce unusually high proportions of normal (or unbranched) aldehydes from α-olefins, e.g., n-butyraldehyde from propylene.

DETAILED DESCRIPTION OF THE INVENTION

In accordance with the present invention, there is provided a process for preparing a bidentate ligand of the formula:

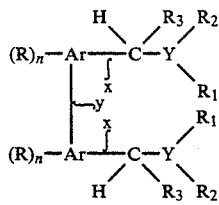

wherein:
each Ar is independently selected from aromatic ring compounds having 6 up to 14 carbon atoms, e.g., phenyl, naphthyl, phenanthryl and anthracenyl;
the x bonds and the y bonds are attached to adjacent carbon atoms on the ring structure;
each R, when present as a substituent, is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl, cyano or formyl radicals;
n is a whole number in the range of 0-4 were Ar is phenyl; 0-6 where Ar is naphthyl; and 0-8 where Ar is phenanthryl or anthracenyl;
each $R_1$ and $R_2$ is independently selected from alkyl, aryl, aralkyl, alkaryl or cycloaliphatic radicals or substituted derivatives thereof;
each $R_3$ is independently selected from hydrogen and the $R_1$ substituents;
each of the above alkyl groups or moieties is a straight or branched chain radical having 1-20 carbons;
each aryl group contains 6-10 ring carbons;
each cycloaliphatic group contains from 4-8 ring carbons;
each Y is independently selected from the elements N, P, As, Sb and Bi; and
substituted derivatives thereof include alkoxy, aryloxy, alkoxyalkyl, halogen, alkanoyl, alkanoyloxy, alkoxycarbonyl, cyano, carboxyl and formyl substituted compounds.

The invention process comprises:
A process for preparing the above-described bidentate ligand comprising the steps,
(1) contacting with ozone under ozonolysis conditions a suspension in a hydroxylic reaction medium of a reactant selected from phenanthrene or a phenanthrene derivative having the structure:

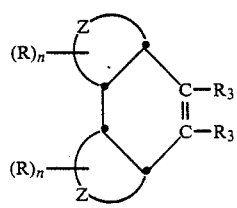

wherein each Z is independently a 4 through 12 carbon fragment completing a single aromatic ring or a fused ring system, respectively, to form an ozonated intermediate;

(2) contacting said ozonated intermediate with a reducing agent under conditions appropriate to form a diol having the structure:

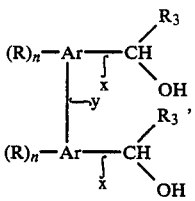

(3) contacting said diol with a latent displaceable functional group under conditions sufficient to convert the diol to a difunctional biphenyl compound having the structure:

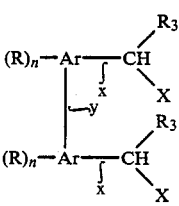

wherein X is a functional group which can be displaced under nucleophilic substitution conditions, and (4) contacting said difunctional biphenyl compound with an anion having the structure:

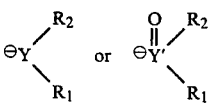

wherein Y' is selected from the group consisting of P, As, Sb and Bi; and Y, $R_1$ and $R_2$ are as defined above;

in a molar ratio of anion to difunctional biphenyl compound in the range of about 1/1 up to 20/1 under conditions appropriate to form the above bidentate ligand.

It is recognized, of course, that in order to obtain the desired bidentate ligand, the initially formed condensation product will require an additional reduction step when the oxy-anion is employed as the source of the P, As, Sb or Bi moiety.

Exemplary functional groups from which X can be selected include the following functional groups:
halogens;
OZ, wherein Z is selected from alkyl, aryl, aralkyl, alkaryl, alkanoyl, aroyl or cycloaliphatic radicals or substituted derivatives thereof; and the like.
tosylate;
mesylate;
brosylate; and
triflate.

In a particular embodiment, the bidentate ligands prepared in accordance with the invention process are compounds of the formula:

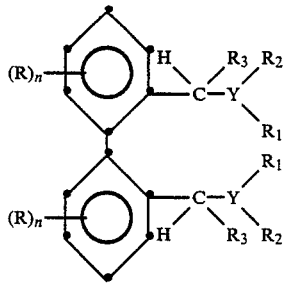

wherein:
n is 0-4;
each R is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl or formyl radicals;
each $R_1$ and $R_2$ is independently selected from alkyl, aryl, aralkyl, alkaryl or cycloaliphatic radicals or substituted derivatives thereof;
each $R_3$ is independently selected from hydrogen and the $R_1$ substituents;
each of the above alkyl groups or moieties is straight or branched chain of 1–20 carbons, each aryl group contains 6–10 ring carbons, and each cycloaliphatic group contains from 4–8 ring carbons;
each Y is independently selected from the elements N, P, As, Sb and Bi, with P being preferred; and
substituted derivatives thereof include alkoxy, aryloxy, alkoxyalkyl, halogen, alkanoyl, alkanoyloxy, alkoxycarbonyl, cyano, carboxyl and formyl substituted compounds.

In another particular embodiment, the bidentate ligands prepared in accordance with the invention process are compounds of the general formula:

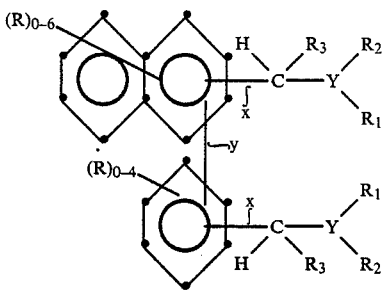

wherein:
the x bonds and the y bonds are attached to adjacent carbon atoms on the ring structures;
each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl or formyl radicals;
each $R_1$ and $R_2$ is independently selected from alkyl, aryl, aralkyl, alkaryl or cycloaliphatic radicals or substituted derivatives thereof;
each $R_3$ is independently selected from hydrogen and the $R_1$ substituents;
each of the above alkyl groups or moieties is straight or branched chain of 1–20 carbons, preferably 1–8 carbons, each aryl group contains 6–10 ring carbons, and each cycloaliphatic group contains from 4-8 ring carbons;

each Y is independently selected from the elements N, P, As, Sb and Bi, with P being preferred; and substituted derivatives thereof include alkoxy, aryloxy, alkoxyalkyl, halogen, alkanoyl, alkanoyloxy, alkoxycarbonyl, cyano, carboxyl and formyl substituted compounds.

In yet another particular embodiment, the bidentate ligands prepared in accordance with the invention process are compounds of the general formula:

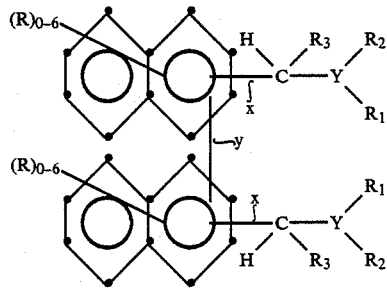

wherein:
the x bonds and the y bonds are attached to adjacent carbon atoms on the ring structure;
each R when present as a substituent is independently selected from alkyl, alkoxy, aryloxy, aryl, aralkyl, alkaryl, alkoxyalkyl, cycloaliphatic, halogen, alkanoyl, alkanoyloxy, alkoxycarbonyl, cyano, carboxyl or formyl radicals;
each $R_1$ and $R_2$ is independently selected from alkyl, aryl, aralkyl, alkaryl or cycloaliphatic radicals or substituted derivatives thereof;
each $R_3$ is independently selected from hydrogen and the $R_1$ substituents;
each of the above alkyl groups or moieties is straight or branched chain of 1-20 carbons, preferably 1-8 carbons, each aryl group contains 6-10 ring carbons, and each cycloaliphatic group contains from 4-8 ring carbons;
each Y is independently selected from the elements N, P, As, Sb and Bi, with P being preferred; and
substituted derivatives thereof include alkoxy, aryloxy, alkoxyalkyl, halogen, alkanoyl, alkanoyloxy alkoxycarbonyl, cyano, carboxyl and formyl substituted compounds.

Especially preferred compounds which can be prepared in accordance with the invention process include:

2,2'-bis(diphenylphosphinomethyl)-1,1'-diphenyl (hereinafter, BISBI);
2,2'-bis(dibenzylphosphinomethyl)-1,1'-biphenyl;
2,2'-bis(phenylbenzylphosphinomethyl)-1,1-biphenyl;
2,2'-bis(diisobutylphosphinomethyl)-1,1'-biphenyl;
2-(diphenylphosphinomethyl)-1-[2-(diphenylphosphinomethyl)phenyl]napththalene; and
2,2'-bis(diphenylphosphinomethyl)-1,1'-binaphthyl.

The ozonolysis reaction is carried out with the phenanthrene or phenanthrene derivatives starting material dispersed in a hydroxylic solvent. Suitable hydroxylic solvents are those which are fluid at room temperature for each of handling, e.g., an alcohol having in the range of 1 up to 6 carbon atoms. Optionally, a cosolvent can also be employed. Suitable cosolvents are those which are nonreactive under ozonolysis reaction conditions and which, when combined with the hydroxylic solvent, remain fluid under ozonolysis reaction conditions. Suitable cosolvents include aromatics, such as for example, benzene, toluene, and the like; halogenated aromatics, such as for example, chlorobenzene, dichlorobenzene, and the like; halogenated hydrocarbons, such as for example, methylene chloride, chloroform, and the like; esters, such as for example, ethyl acetate, methyl acetate, and the like; aliphatic hydrocarbons, such as for example, pentane, hexane and the like; and so on.

The concentration (in g/L) of phenanthrene or phenanthrene derivative in the ozonolysis reaction medium can vary over a wide range, with concentrations up to about 200 g/L being suitable. Preferably, the concentration of phenanthrene or phenanthrene derivative will fall within the range of about 20 up to 175 g/L with a concentration in the range of about 50 up to 150 g/L being most preferred.

The volumetric ratio of cosolvent to hydroxylic solvent employed can vary widely, i.e., from 0 up to about 20:1, with a volumetric ratio in the range of 1:1 up to 10:1 being preferred. The amount of hydroxylic solvent employed should be at least 2 moles per mole of phenanthrene or phenanthrene derivative, with any quantity in excess of this ratio being suitable.

A preferred reaction medium for the ozonolysis step is a mixture of a chlorinated aliphatic hydrocarbon, e.g., methylene chloride or chloroform, with an alcohol having 1 up to 4 carbon atoms in a volumetric ratio in the range of about 1:1 up to 10:1.

The ozonolysis reaction can suitably be carried out over a wide temperature range. Temperatures as low as about −100° C. up to room temperature (about 25° C.) are suitable. Preferably, reduced temperatures in the range of about −100° C. up to −20° C. will be employed, with temperatures in the range of about −85° up to −50° C. being most preferred, because byproduct formation is minimized at such reduced temperatures.

Reaction time for the ozonolysis reaction is a function of numerous variables, but typically reactions will be carried out for sufficient time to allow essentially complete consumption of the phenanthrene or phenanthrene derivative starting material. Such variables as reaction temperature, reaction pressure, concentration and rate of ozone introduction into the reaction medium, concentration of phenanthrene or phenanthrene derivative in the reaction medium, rate of mixing, efficiency of ozone dispersion, and the like, will affect the time required for essentially complete consumption of starting materials.

The ozonolysis reaction can be carried out over a wide range of pressures, as the reaction pressure is not a critical reaction parameter. Typically, reaction will be carried out at atmospheric pressure, while those of skill in the art recognize that both higher and lower pressures are suitable, with higher pressures having the advantage of allowing the generation of higher ozone concentrations in solution.

Conversion of the ozonated intermediate to the corresponding diol can be promoted by a variety of reducing agents, such as for example, borohydride compounds which conform to the formula:

$$M(FH_4)_n$$

where M is a monovalent or divalent cation selected from the group consisting of quaternary ammonium cations ($NR_4$-wherein each R is independently $C_1$ through $C_{10}$ alkyl, cycloalkyl, aryl, aralkyl and alkaryl), alkaline earth metals and alkali metals. Where M is a monovalent cation, n=1. Where M is a divalent cation, n=2. Examples of useful borohydride compounds include lithium borohydride, sodium borohydride, potassium borohydride, magnesium borohydride, calcium borohydride, and tetraethyl ammonium borohydride.

Additional suitable reducing agents include aluminum hydrides which conform to the formula:

wherein M' is lithium or sodium, R is selected from the group consisting of H or alkoxy and x is an integer ranging from 0 up to 3. Those of skill in the art recognize that additional quantities of hydride reducing agent will be required where excess hydroxylic solvent remains in the reaction mixture; or alternatively, the excess hydroxylic solvent used for the ozonolysis reaction would desirably be removed prior to the reduction step.

In addition, catalytic hydrogenation in the presence of catalysts such as palladium on carbon can also be employed for the desired reduction.

The temperature at which the reduction reaction is carried out can vary over wide ranges. Reduction temperatures as low as about $-50°$ up to about 100° C. are suitable. Preferably, temperatures in the range of about $-10°$ up to 60° C. will be employed, with a reduction temperature in the range of about 0° up to 40° C. being most preferred because the reduction reaction is very slow at excessively low temperatures, with undesirably high levels of by-products obtained when higher reaction temperatures are employed.

The pressure at which the reduction reaction is carried out is not critical, and thus reduction can be carried out over a wide range of pressures. Generally, reduction is carried out at atmospheric pressure, although both higher and lower pressures are suitable. Superatmospheric reaction pressures are preferred when catalytic reduction is carried out to produce the diol.

The amount of time for which the reduction reaction is carried out is a function of numerous reaction parameters and can readily be determined by those of skill in the art. For example, the borohydride reduction is generally quite fast, and requires very short reaction times, e.g., reaction can be worked up shortly after all reducing agent has been added to the reaction mixture.

It is of note with respect to each of the reaction parameters already discussed that reduction can be carried out in two stages, such that the ozonated intermediate is initially reduced only to the aldehyde stage, with further reduction then being carried out under more vigorous reaction conditions to provide the desired diol.

In a preferred embodiment of the present invention, the reduction of the ozonated intermediate is accomplished by adding the ozonolysis reaction mixture of about $-78°$ C. to a solution of sodium borohydride in ethanol at a temperature in the range of 15° C. to 25° C. The reaction is exothermic and the temperature of the reaction mixture is maintained at the desired level by means of an external bath. This procedure for the preparation of the diol typically gives yields in the range of 93 to 95 percent of theory.

The next step of the invention process involves "activating" the benzylic carbon atom towards nucleophilic substitution. This typically involves converting the diol to a difunctional biaryl derivative having the structure:

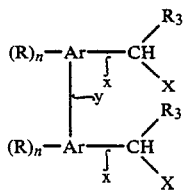

wherein the functional groups, X, are good leaving groups under nucleophilic reaction conditions. Thus, the hydroxy groups of the diol compound can be replaced with halogens, tosylates, brosylates, triflates, mesylate, trifluoroacetate, —OZ, wherein Z is selected from alkyl, aryl, aralkyl, alkaryl, alkanoyl, aroyl or cycloaliphatic radicals or substituted derivatives thereof; and the like.

Those of skill in the art have available numerous reagents which can suitably be employed for the desired activation of the benzylic carbon atom. Thus, halogenating agents such as aqueous hydrobromic acid, anhydrous hydrogen bromide, thionyl chloride, phosphorus trihalides, e.g., $PBr_3$, $Ph_3P—Br_2$; $Ph_3P—CBr_4$; $Ph_3P—CCl_4$ perhalogenated metal compounds, e.g., $SnBr_4$, $TiCl_4$; $PCl_5$; and the like can be employed. Alternatively, the benzylic carbon of the diol can be activated by reacting the diol in the presence of base with paratoluene sulfonyl chloride (to form the tosylate), with methane sulfonyl chloride (to form the mesylate), with trifluoromethane sulfonyl chloride or trifluoromethane sulfonic anhydride (to form the triflate), with methyl iodide, dimethyl sulfate or other alkylating agents (to form an alkyl ether), with acetyl chloride, acetic anhydride, trifluoroacetic anhydride, and the like (to form an ester), and the like. Presently preferred activating agents are thionyl chloride and phosphorus tribromide, as these reagents are readily available, relatively inexpensive, and give excellent conversion of diol to the activated compound.

The temperature at which the activation of the benzylic carbon atom can be carried out can vary widely. Temperatures as low as about $-80°$ C. up to about 150° C. can be employed. Preferably, temperatures in the range of about $-20$ up to 100° C. are employed, with temperatures in the range of about $-10$ up to 40° C. most preferred.

The conversion of the "activated" difunctional biaryl compound to the desired bidentate ligand is carried out by contacting the activated compound with an anion of the formula:

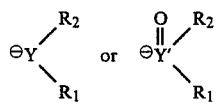

where Y' is selected from the group consisting of P, As, Sb and Bi; and Y, $R_1$ and $R_2$ are as defined above.

It is recognized, of course, that in order to obtain the desired bidentate ligand, the initially formed condensation product will require an additional reduction step when the oxy-anion is employed as the source of the P, As, Sb or Bi moiety.

The above anions can be associated with a variety of cations, typically alkali metals which were employed for the preparation of the anion. For example, the diphenylphosphide anion can be prepared by treating diphenylphosphine with n-butyllithium in ether or THF. Since the resulting anion is a brightly colored species (yellow in ether and orange in THF), the disappearance of color, or a change in the color of the reaction mixture can frequency be used as an indicator of the progress of the activated difunctional biaryl compound/anion reaction.

An alternate method for the preparation of lithio diphenylphosphine anion is to prepare and use the anion in-situ by means of the reductive cleavage of triphenylphosphine to phenyl lithium and the desired diphenylphosphine anion. The phenyllithium which is produced should preferably be quenched prior to the addition of the activated difunctional biaryl compound to the solution. The most effective means to quench the reaction is the addition of an equivalent amount of tertiary butyl chloride, which undergoes a dehydrohalogenation reaction to give benzene, lithium chloride, and isobutylene.

Suitable temperatures for reaction between the activated difunctional biaryl compound the above described anion can vary over a wide range. Typically, temperatures in the range of about $-80°$ up to $150°$ C. will be employed. Preferably, temperatures in the range of about $-10°$ up to $100°$ C. will be employed, with temperatures in the range of about $10°$ up to $60°$ C. being most preferred, because acceptable reaction rates are obtained at such temperatures while the formation of by-products is minimized.

The ratio of anion to difunctional biaryl compound employed will vary in the range of about 1.5:1 up to about 4:1. The use of even lower ratios is undesirable as the presence of significant quantities of unreacted starting material difunctional biaryl compound could lead to the formation of quaternary salts whose presence in the reaction mixture is undesirable. On the other hand, the use of substantially greater amounts than the 4:1 ratio recited above will simply produce large quantities of the reduced anion which would need to be recovered and disposed of or recycled as appropriate. Consequently, preferred ratios of anion to activated difunctional biaryl compound fall within the range of 1.9:1 up to 2.5:1, with ratios in the range of 2.0:1 up to 2.2:1 being most preferred.

In order to minimize the occurrence of side reactions, it is preferred that the activated difunctional biaryl compound be added to a solution containing the anion. The reverse order of addition is less desirable because such mode of addition would lead to the formation of significant quantities of quaternary compounds.

The reaction between activated difunctional biaryl compound and anion can be carried out in a wide range of solvents, such as for example, ethers (e.g., tetrahydrofuran, diethylether, and the like), aprotic solvents (such as, for example, the glymes, e.g., diglyme, triglyme, and the like; saturated hydrocarbons, such as pentane, hexane, heptane, and the like; aromatic hydrocarbon solvents, e.g., benzene, toluene, zylene, and the like).

As well known by those of skill in the art, it is preferred that all manipulations involving Group VA compounds (i.e., compounds of P, As, Sb and Bi), especially compounds of phosphorus, be carried out under an inert atmosphere, e.g., $N_2$, Ar, etc.

It is particularly noted that during the above reactions, the concentrations of the various reactant materials and their ratios as set forth above will necessarily change and it is preferred for any continuous process involving these reactions that the concentrations be maintained at least within the specified broad ranges by addition of reactants to the reaction mixture as is necessary.

It is also noted with respect to the above stated reaction conditions, that the temperatures employed for any step will be dictated to a degree by the particular reactants employed, and also by the size and design of the equipment. For example, the thermal stability of the particular materials in the reaction mixture must be considered and any exotherm monitored to prevent degradation or excessive side reactions. The reaction pressures for all conversion steps described herein need only be ambient. Lower or higher pressures give no significant enhancement to the reactions and typically are not warranted, except for such reactions as $H_2$ reduction with which pressure may desirably be employed.

In regard to the isolation and work-up of the various intermediate products, as well as the desired bidentate ligand product, the procedure generally involves such steps as distillation, solvent wash and extraction, recrystallization, filtering, aqueous washing and drying under vacuum. It is particularly noted however, that for the present materials, work-up presents no difficulty and the target products are readily obtained in good yield and excellent purity.

The following examples will further illustrate the present invention:

EXAMPLE 1

Ozonolysis of Phenanthrene to 2,2'-Bis(hydroxymethyl)-1,1'-biphenyl

To a reaction system comprising a suspension of phenanthrene (89.12 grams, 0.5 mole) in methylene chloride (650 mL) and ethanol (150 mL) at dry ice temperature (about $-78°$ C.) was added a combined stream of dry air and ozone. The ozone was generated in a Welsback ozone generator which produced about 63 mmoles of ozone per hour. The ozone/air stream was bubbled through the reaction system until a persistent blue color appeared. The system was then purged of excess ozone with nitrogen and then added in small portions (at dry ice temperatures) to a solution of sodium borohydride (17.01 grams, 0.45 mole) in ethanol (1 liter) at $15°$ C. to $25°$ C. External cooling was required to maintain the temperature of the ethanol solution. Upon completion of the addition, the reaction was stirred overnight, heated on a steam bath and stripped to a thick residue under a stream of nitrogen. The residue was carefully treated with 50 mL of concentrated hydrochloric acid (HCl), diluted in 50 mL of water, and then diluted to 5 liters with water and ice. The product precipitated as a white powder which was filtered and dried in a vacuum desiccator to give 99.2 grams (93 percent yield).

EXAMPLE 2

Preparation of 2,2'-Bis(chloromethyl)-1,1'-biphenyl

Using Thionyl Chloride

To a reaction system comprising a suspension of 2,2'-bis(hydroxymethyl)-1,1'-biphenyl (85.3 grams, 0.398 mole) in methylene chloride (500 mL) at $0°$ C. containing pyridine (2 mL) was added a solution of thionyl chloride (163 grams, 1.36 moles) in methylene chloride (100 mL) dropwise with stirring. The system was allowed to warm to room temperature overnight and then was stripped to a residue with a stream of nitrogen at room temperature. The residue was dissolved in toluene (100 mL), cooled to 0° C., and quenched by the addition of ice cold, saturated sodium chloride solution (100 mL). The layers were separated, the organic phase was washed with water at 0° C. (1×100 mL), the layers separated, and the organic phase dried with magnesium sulfate. The solvent was evaporated to give a thick oil which was then distilled at 125° C. to 127° C. (0.1 mm Hg) to give 91.9 grams of colorless oil which contained 71.3 g of product dichloride (71% of theoretical yield).

EXAMPLE 3

Preparation of 2,2'-Bis(bromomethyl)-1,1'-biphenyl Using Phosphorus Tribromide 2,2'-Bis(hydroxymethyl)-1,1'-biphenyl (25.0 grams, 0.117 mole) and methylene chloride (200 mL) were placed in a 500-mL round-bottomed flask equipped with a magnetic stirrer and an addition funnel with a CaCl$_2$ drying tube. The stirred mixture was cooled with an ice bath, and phosphorus tribromide (23.1 mL, 66.50 grams, 0.246 mole) was added dropwise from the addition funnel. After the addition was complete, the reaction mixture was removed from the ice bath and stirred overnight at room temperature. The mixture was again cooled with an ice bath, and water (35 mL) was added slowly. After stirring for 1 hour, additional water (75 mL) was added. The layers were separated in a separatory funnel, and the aqueous layer was extracted twice with CH$_2$Cl$_2$. The combined organic layer was first washed with saturated aqueous NaHCO$_3$ and then water, and then dried (MgSO$_4$). The solvent was removed on a rotary evaporator to give 37.05 grams (93 percent yield) of light yellow solid which was suitable for use without further purification. The melting point was 85° C. to 88° C.

EXAMPLE 4

Preparation of BISBI From 2,2'-Bis(chloromethyl)-1,1'-biphenyl and Triphenylphosphine To a 5-liter flask equipped with mechanical stirrer, thermowell, addition funnel, and condenser was added triphenylphosphine (167.7 grams, 0.640 mole), THF (640 mL), and lithium wire (8.88 grams, 1.28 mole). The flask was cooled by external cooling to maintain an internal temperature of 15° C. to 25° C. The reaction was then stirred overnight which resulted in the dissolution of nearly all of the lithium. The flask was cooled to 10° C. and tertiary butyl chloride (59.2 grams, 0.640 mole) was added over a 1-hour period while the temperature was held below 30° C. with a water bath. Upon completion of the addition, the reaction was heated to 40° C. for 0.5 hour and then cooled to −10° C. 2,2'-Bis (chloromethyl)-1,1'-biphenyl reactant (103 grams of 73% pure material, i.e., 75 g of the reactant, 0.320 mole) in THF (200 mL) was added dropwise to the solution of the anion and heated to reflux for 0.5 hour after completion of the addition. The reaction mixture was cooled to room temperature and then quenched by the addition of methanol (40 mL). The apparatus was then equipped with a distillation head and 0.9 liter of the reaction solvent was removed. During the distillation, the base temperature rose to 85° C. and was then cooled back to ambient. A liter of diethyl ether was then added followed by the addition of one liter of degassed water. The mixture was stirred, the layers separated, and the organic phase water washed (3×500 mL) with layer separation. The final ether layer was stripped to dryness under vacuum to give the crude product. This product was recrystallized from a THF/methanol mixture (220 mL THF with 1.60 liters of methanol), filtered and washed with cold methanol. The product BISBI was dried under high vacuum to give 138.9 grams (84.5 percent of theory) of BISBI as a white powder.

The invention has been described in detail with particular reference to preferred embodiments thereof, but it will be understood that variations and modifications will be effected within the spirit and scope of the invention.

I claim:

1. A process for preparing a bidentate ligand of the formula

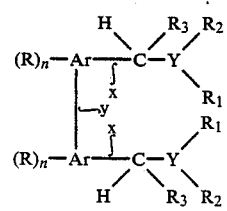

wherein
- each Ar is independently selected from aromatic ring compounds having 6 up to 14 carbon atoms;
- the x bonds and the y bonds are attached to adjacent carbon atoms on the ring structures;
- each R, when present as a substituent, is independently selected from alkyl, alkoxy, aryloxy, aryl, aralkyl, alkaryl, alkoxyalkyl, cycloaliphatic, halogen, alkanoyl, alkanoyloxy, alkoxycarbonyl, carboxyl, cyano or formyl radicals;
- n is a whole number in the range of 0–4 where Ar is phenyl; 0–6 where Ar is naphthyl; and 0–8 where Ar is phenanthryl or anthracenyl;
- each R$_1$ and R$_2$ is independently selected from alkyl, aryl, aralkyl, alkaryl or cycloaliphatic radicals or substituted derivatives thereof; wherein substituted derivatives thereof are selected from alkoxy, aryloxy, alkoxyalkyl, halogen, alkanoyl, alkanoyloxy, alkoxycarbonyl, cyano, carboxyl or formyl substituted compounds;
- each R$_3$ is independently selected from hydrogen and the R$_1$ substituents;
- each of the above alkyl groups or moieties is a straight or branched chain of 1–20 carbons; preferably 1–8 carbons;
- each aryl group contains 6–10 ring carbons;
- each cycloaliphatic group contains from 4–8 ring carbons; and
- each Y is independently selected from the elements N, P, As, Sb and Bi;

said process comprising the steps,
  (1) contacting with ozone under ozonolysis conditions a suspension in a hydroxylic reaction medium of a reactant selected from phenanthrene or a phenanthrene derivative having the structure:

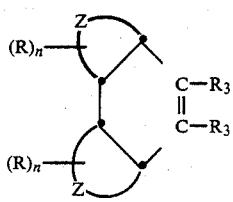

wherein each Z 4 through 12 carbon fragment completing a single aromatic ring or a fused ring system, respectively, to form an ozonated intermediate;

(2) contacting said ozonated intermediate with a reducing agent under conditions appropriate to form a diol having the structure:

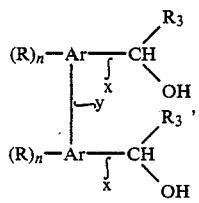

(3) contacting with diol with an activating agent comprising a latent displaceable functional group, X, under conditions sufficient to convert the diol to a difunctional biaryl compound having the structure:

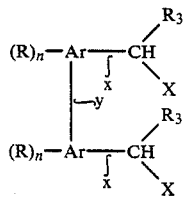

wherein X is a functional group which can be displaced under nucleophilic substitution conditions, (4) contacting said difunctional biaryl compound with an anion having the structure:

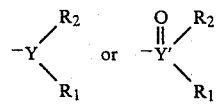

wherein Y' is selected from the group consisting of P, As, Sb and Bi;
in a molar ratio of anion to difunctional biaryl compound in the range of about 1/1 up to 20/1 under conditions appropriate to displace X and thereby form the above bidentate ligand or an oxygenated intermediate product thereof; and (5) optionally reducing the oxygenated intermediate product when the oxy-anion,

is employed as the anion in step (4).

2. The process of claim 1 wherein the reactant of step (1) is phenanthrene.

3. The process of claim 1 wherein the hydroxylic solvent is an alcohol having in the range of 1 up to 6 carbon atoms.

4. The process of claim 3 wherein a cosolvent is also employed, said cosolvent being selected from the group consisting of:
aromatic compounds,
halogenated aromatic compounds,
halogenated aliphatic compounds,
esters,
aliphatic hydrocarbons,
and mixtures of any two or more thereof.

5. The process of claim 1 wherein the liquid reaction medium for step (1) is a mixture of a chlorinated aliphatic compound and an alcohol having in the range of 1 up to 6 carbon atoms.

6. The process of claim 1 wherein the hydroxylic reaction medium for step (1) is a mixture of methylene chloride and an alcohol having in the range of 1–4 carbon atoms.

7. The process of claim 4 wherein the volumetric ratio of cosolvent to hydroxylic solvent falls within the range of about 1:1 up to 10:1.

8. The process of claim 6 wherein the volumetric ratio of methylene chloride to alcohol falls within the range of about 1:1 up to 10:1.

9. The process of claim 1 wherein the said reaction medium is maintained at a temperature in the range of about −100° C. up to 25° C.

10. The process of claim 1 wherein step (22) is carried out at a temperature in the range of about −50° C. to about 100° C.

11. The process of claim 10 wherein said reducing agent is selected from the group consisting of:
borohydride compounds of the formula:

M(BH$_4$)$_n$ wherein M is a monovalent or divalent cation; with n=1 when M is a monovalent cation and n=2 when M is a divalent cation; and
aluminium hydrides of the formula:

M'ALH$_{4-x}$R$_x$ where M' is lithium or sodium, R is H or alkoxy and x is an integer ranging from 0 up to 3.

12. The process of claim 10 wherein the reducing agent is a solution of sodium borohydride in ethanol at a borohydride concentration in the range of about 0.1 g-mol up to 2.0 g-mol per of liter ethanol.

13. The process of claim 10 wherein the reaction mixture of step (1) is added to a solution of the reducing agent.

14. The process of claim 1 wherein the activating agent of step (3) is selected from the group consisting of:
thionyl chloride,
phosphorus trihalides;
Ph$_3$P—Br$_2$complex;

Ph₃P—CBr₄;
Ph₃P—CCl₄;
perhalogenated metal compounds;
PCl₅;
paratoluene sulfonyl chloride;
methanesulfonyl chloride trifluoromethane sulfonyl chloride; trifluoromethane sulfonic anhydride; methyl iodide;
dimethyl sulfate;
acetyl chloride;
acetic anhydride;
benzoyl chloride;
trifluoroacetic anhydride;
aqueous hydrobromic acid, and anhydrous hydrogen bromide in methylene chloride.

15. The process of claim 14 wherein the reaction mixture is maintained at a temperature in the range of about −80° C. up to 100° C.

16. The process of claim 1 wherein said latent displaceable functional group, X, is selected from the group consisting of:
halogens;
OZ, wherein Z is selected from alkyl, aryl, aralkyl, alkaryl, alkanoyl, aroyl or cycloaliphatic radicals or substituted derivatives thereof; wherein substituted derivatives thereof are selected from alkoxy, aryloxy, alkoxyalkyl, halogen, alkanoyl, alkanoyloxy, alkoxycarbonyl, cyano, carboxyl or formyl substituted compounds;
tosylates;
brosylates;
triflates;
mesylates; and
trifluoroacetates.

17. The process of claim 16 wherein said latent displaceable functional group is selected from the group consisting of:
halogens,
tosylates,
brosylates,
triflates,
mesylates, and
trifluoroacetates.

18. The process of claim 1 wherein the activating agent of step (3) is a solution of thionyl chloride in methylene chloride containing a trace of pyridine, maintained at a temperature in the range of about −10° C. up to 40° C.

19. The process of claim 1 wherein said anion employed in step (4) is a dihydrocarbylphosphide anion.

20. The process of claim 19 wherein said anion is present as the anion of an alkali metal salt of diphenylphosphine.

21. The process of claim 17 wherein said anion is formed by the reductive cleavage of triphenylphosphine with lithium metal at a temperature in the range of about 5° C. up to 40° C.

* * * * *

UNITED STATES PATENT AND TRADEMARK OFFICE
CERTIFICATE OF CORRECTION

PATENT NO. : 4,879,416

DATED : November 7, 1989

INVENTOR(S) : Thomas A. Puckette et al

It is certified that error appears in the above-identified patent and that said Letters Patent is hereby corrected as shown below:

Claim 1, Column 13, line 12, after "Z" and before "4" please insert ---is independently a---.

Claim 1, Column 13, line 31, delete "with" and insert therefor ---said---.

Claim 10, Column 14, line 39, delete "(22)" and insert therefor ---(2)---.

Claim 11, Column 14, line 53, delete "M'ALH$_{4-x}$R$_x$" and insert therefor ---M'AlH$_{4-x}$R$_x$---.

Signed and Sealed this

Twelfth Day of November, 1991

Attest:

HARRY F. MANBECK, JR.

*Attesting Officer*   *Commissioner of Patents and Trademarks*